United States Patent [19]

Campbell

[11] Patent Number: 4,862,903

[45] Date of Patent: Sep. 5, 1989

[54] BREATHING MOUTHPIECE FOR CONTACTING UPPER PALATE AND LOWER JAW OF USER'S MOUTH

[75] Inventor: Steven M. Campbell, Laguna Beach, Calif.

[73] Assignee: U.S. Divers Company, Inc., Santa Ana, Calif.

[21] Appl. No.: 106,388

[22] Filed: Oct. 9, 1987

[51] Int. Cl.[4] .................... A61F 5/56

[52] U.S. Cl. .................... 128/861; 128/200.29; 128/201.11; 128/206.29

[58] Field of Search .................... 128/200.29, 201.11, 128/201.26, 201.27, 202.28, 204.26, 206.29, 136, 207.14

[56] References Cited

U.S. PATENT DOCUMENTS

| | | | |
|---|---|---|---|
| 2,521,084 | 9/1950 | Oberto | 128/206.29 |
| 2,589,504 | 3/1952 | Miller | 128/136 |
| 2,669,988 | 2/1954 | Carpenter | 128/136 |
| 2,839,053 | 6/1958 | Lorenz | 128/206.29 |
| 3,107,667 | 10/1963 | Moore | 128/136 |
| 3,126,002 | 3/1964 | Owens | 128/136 |
| 3,467,091 | 9/1969 | Aragona | 128/201.11 |
| 3,603,306 | 9/1971 | Bonin, Jr. | 128/201.11 |
| 4,664,109 | 5/1987 | Rasocha | 128/201.11 |

*Primary Examiner*—Max Hindenburg
*Assistant Examiner*—J. P. Lacyk
*Attorney, Agent, or Firm*—George F. Bethel; Patience K. Bethel

[57] ABSTRACT

The specification sets forth a mouthpiece for use with a snorkel or regulator of the type used in diving and life support systems. The mouthpiece is attached to a snorkel or regulator by a conduit and terminates in a lip flange for seating within the upper and lower lips. Extending between the lip flange is an upper palate web that conforms to the palate area of a user's mouth. Within the palate web is an opening toward the frontal area for receipt of a user's front teeth. The mouthpiece incorporates a lower web that extends along the inner jaw region overlying the inner portion of a user's lower teeth. The lower web can be split in its conformation with a gap therebetween formed by two tabs that are rounded at their ends. The entire mouthpiece conforms and holds the snorkel or regulator in a user's mouth in a facile manner without the requirement of excessive biting and eliminates prior art lugs or bits.

23 Claims, 4 Drawing Sheets

BREATHING MOUTHPIECE FOR CONTACTING UPPER PALATE AND LOWER JAW OF USER'S MOUTH

FIELD OF THE INVENTION

The field of this invention lies within the diving and regulator art. In particular, it lies within the art of second stage breathing gas regulators for divers and mouthpieces pertaining thereto.

BACKGROUND OF THE INVENTION

The prior art with regard to divers' breathing gas regulators comprises a number of regulators that have been configured in various mechanical forms to provide balanced regulation, normal regulation without balance, and related fluid mechanical features for ease of breathing. Other regulators have provided a pilot function so that upon initiation of a breath, the regulator changes from one mode to another for piloting the movement of a second stage regulator piston. Also, regulators have incorporated various features as to the fluid mechanical aspects thereof to create easier breathing and greater functionality with regard to the regulation of the intermediate pressure gas being delivered from the first stage regulator.

In all the prior art regulators and snorkels, little or no attention has been paid to the mouthpiece. Generally, the mouthpiece follows the standard mouthpiece that has been known over the years. This can be exemplified by the mouthpiece shown in the patent to Bonin, U.S. Pat. No. 3,603,306. In this particular patent there are shown lugs, or biting tabs upon which a user engages the mouthpiece.

An attempt has been made to provide for a more easily held mouthpiece as disclosed in Shamlain's patent, U.S. Pat. No. 3,844,281. This particular patent incorporates the concept of utilizing a conformable thermoplastic material. Thermoplastic material is placed over the lugs or biting tabs that a user normally engages a second stage regulator with. The thermoplastic material is conformably heatset by a user biting into the plastic material when heated.

A further attempt and advance was made by the teaching shown in the Cerniway patent, U.S. Des. Pat. No.246,671. In that patent, the showing was of a second stage regulator mouthpiece. In that case, the entire mouthpiece incorporated a block of thermoplastic material upon which a user could bite down and cause it to conform to the teeth.

In all of the foregoing prior art patents, a solution was not at hand with regard to a comfortable fit of a mouthpiece contoured to the interior surface of a mouth. Also, the facets of the overall requirements for a mouthpiece as demanded in a second stage regulator were not met.

Fundamentally, the prior art mouthpieces all were nothing other than blocks, tabs, or a bit upon which a user could bite. The end result was that the user had to significantly bite into the mouthpiece to keep it in place. This became uncomfortable to the user over an extended period of time. The usage of the Applicant's mouthpiece herein has been shown to be extremely comfortable. Prior art jaw fatigue is substantially decreased. Such jaw fatigue is usually encountered during long durations of diving with conventional mouthpieces.

The regulator weight is distributed throughout the entire mouth in the Applicant's mouthpiece rather than on two discrete bits or in a densely loaded area. The prior art did not function to remedy this so that a load could be spread over the entire oral, mouth or tooth area, but was rather concentrated.

Another deficiency of the prior art was that the air flow was not as well oriented as a user would like. The Applicant's invention has been found to provide for easier breathing. This is as a result of being able to provide a further widening to the mouth and opening of the teeth when they engage the mouthpiece hereof.

The prior art required that a limited amount of teeth be used to keep the mouthpiece in place. When users who did not have teeth in the right place, used the mouthpiece or had a partial plate or full plate, the grip was not effective by the teeth holding the mouthpiece in place.

The jaw fatigue encountered in prior mouthpieces created substantial work upon the part of the diver. This has been one of the drawbacks of prior art mouthpieces as they have been used.

The prior art mouthpieces required a substantial gripping by the mouth to have it close down upon the bits or tabs of the mouthpiece. The invention hereof does not require such action.

In general, the invention hereof provides for the regulator weight to be distributed over a broader area of the entire mouth instead of merely two points. In addition to the foregoing, a user need not bite on the mouthpiece to keep it in place in a vigorous manner as in the prior art. This also eliminates the likelihood that the user will bite through the mouthpiece as in prior art regulators.

Attendant with the improvements hereof is the fact that the spreading of the load makes it less likely that a user's teeth will be damaged upon impact of the regulator. This can be appreciated, inasmuch as divers encounter various conditions when diving which cause the regulator to possibly impact and thereby hit the teeth of the user.

The end result is that jaw fatigue is limited by the invention hereof and the mouthpiece provides optimum comfort by resting on the palate areas as well as the teeth.

The mouthpiece is held more rigidly in place, which makes it difficult to knock out as opposed to the prior art. This also helps to prevent the mouthpiece from falling out as in the prior art.

The mouthpiece can be coupled to or integrally molded with a snorkel to provide an improved snorkel in conjunction with the improved mouthpiece.

As a consequence, this invention is a step over the prior art and will be seen hereinafter as being a significant aid to divers using self-contained underwater breathing apparatus, as well as free diving equipment, such as snorkels and industrial breathing equipment.

SUMMARY OF THE INVENTION

In summation, this invention provides for an improved demand regulator or snorkel mouthpiece having contours and openings which provide for a regulator or snorkel being supported in the mouth of a user in a more facile manner.

The invention comprises a mouthpiece for a second stage regulator or snorkel having contours to fit the interior of the oral cavity. The fitting of a mouthpiece on the interior of the oral cavity is enhanced by a graduated upper surface being angled to fit the upper palate of a user. The lower surface is angled more radically downwardly toward the jaw of a user to conform to a user's lower teeth.

The mouthpiece incorporates two openings formed laterally across the longitudinal orientation of the mouthpiece, for a user's teeth to engage the mouthpiece. These openings allow for a user's teeth to pass into the mouthpiece for ease of breathing and retaining the mouthpiece.

In an alternative embodiment which is deemed to be a preferred embodiment, the lower portion of the mouthpiece is split. The split opening allows for freedom of movement of the tongue of the user in a more facile manner. The split opening also allows for the flexibility of the base of the mouthpiece to retain the mouthpiece in place without covering completely the lower portion of the lower cavity near the jaw on the interior portion of the lower teeth.

The mouthpiece incorporates a conduit with a flange connected to the interior seating portion thereof. The flange allows for a second stage regulator to be clamped and held in place. The end result is a firm and fixed fitting of the entire second stage regulator and eliminates the prior art problems of the second stage regulator being appended to merely two tabs or bits on the second stage regulator mouthpiece.

The mouthpiece can also be connected or molded to a snorkel to provide for an improved snorkel and attendant mouthpiece. The net result is a snorkel with a highly comfortable and functional mouthpiece that serves to provide many of the operational features attendant with the mouthpiece when used with a regulator.

BRIEF DESCRIPTION OF THE DRAWINGS

The invention will be more clearly understood by reference to the description below taken in conjunction with the accompanying drawings wherein.

DESCRIPTION OF THE PREFERRED EMBODIMENTS

Figure 1:
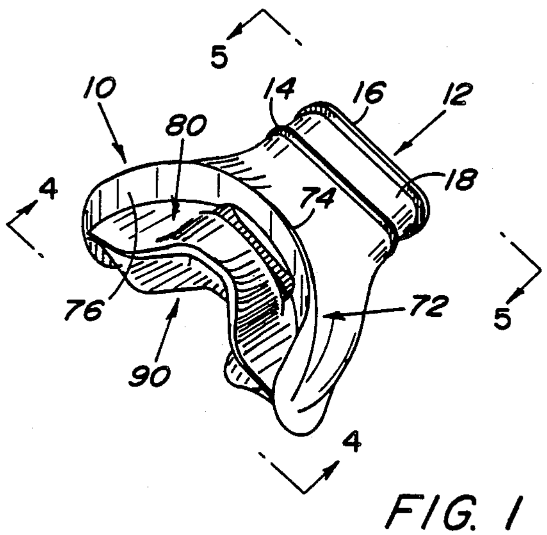
FIG. 1 shows a perspective view of the mouthpiece of a second stage breathing gas regulator which incorporates this invention.

FIG. 1 shows an embodiment of this invention from an upper perspective view. The invention incorporates a mouthpiece configuration generally shown as mouthpiece area 10 which fits in a user's mouth. The mouthpiece flows into a generally rectangular tubular portion 12. The generally rectangular tubular portion 12 incorporates a pair of flanges 14 and 16. The flanges 14 and 16 define a groove 18. The groove 18 provides for maintenance of a regulator air tube shown in FIGS. 7 and 8 as regulator air tube 20. The tube 20 seats in the interior of the tubular conduit section 20. In particular, it is received within tubular conduit section interior portion 22.

A clamp 24 surrounds the grooved tubular portion 18. This clamp 24 is secured by means of a screw or any other tightening means. The clamp 24 can be a metal clamp that is drawn together by means of set screws, threaded advancement means or other means which close the circumference.

The foregoing connection allows for the flow of second stage regulator gas from the second stage regulator generally shown as regulator 28. Regulator 28 incorporates a connection fitting 30 connected to a source of intermediate pressure through hose 32. The source of intermediate pressure through the hose 32 is connected to the fitting 30 by any suitable means, such as the metal connector 34.

The second stage regulator 28 incorporates the known purge valve and diaphragm on a face 38 of the second stage regulator 28. The face 38 is clamped or threaded to the regulator body 40 at the flange.

The body 40 incorporates a tilt valve assembly which valves gas introduced at fitting 30 into the regulator body 40 and thereafter into the conduit or tube 20. This then delivers gas through the opening 22 of the mouthpiece into the mouthpiece portion 10. Exhaust from the mouthpiece is vented through the opening 22 outwardly through two portions of an exhaust manifold shown as portion 46 and portion 48.

Figure 7:
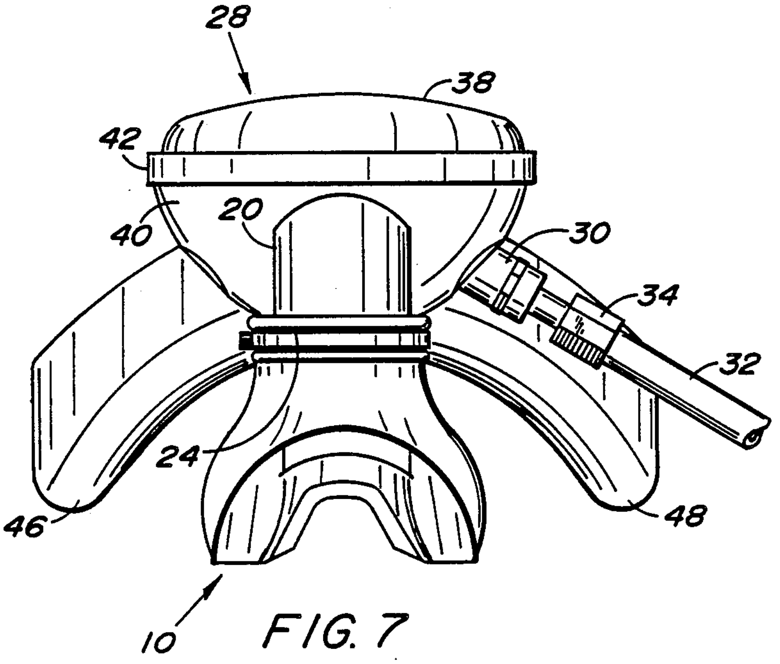
FIG. 7 PRIOR ART
FIG. 7 shows a top plan view of the regulator mouthpiece of this invention with a second stage regulator attached thereto.

The improvement of this invention over the prior art resides within the mouthpiece portion 10. The mouthpiece portion 10 as can be seen in FIG. 7 varies from that of the prior art which has been numbered 10*a*. The prior art shows bits or lugs 56 and 58. The bits or lugs have flange portions respectively 60 and 62.

In order to accommodate securement of the mouthpiece portion 10*a* into a user's mouth, one bites down on the surfaces of the lugs 56 and 58. This creates a situation which allows for securement of the mouthpiece in the user's mouth.

The insert of the tube 20 into the conduit area 12 is enhanced by an enlarged portion of the tube 20 that seats over an interior enlarged portion 70 of passage or opening 22. The interiorly enlarged portion 70 allows for the tube 20 to fit therein. Also, a second enlarged portion can be utilized if necessary which has been shown.

The design of the conduit area 12 is a matter of discretion as to how the entire invention is to be affixed to the tube 20 of a regulator.

Looking specifically at the mouthpiece portion 10 in FIGS. 1 through 8, it can be seen that a lip flange 72 is shown. The lip flange 72 is an area of the mouthpiece that is contoured to fit the interior portions of the lips. It comprises an exterior lip portion 74 and an interior lip portion 76. The interior lip portion 76 seats against the teeth of a user so as to accommodate the mouthpiece against a user's teeth. The exterior lip portion 74 seats against the inner portion of the lips so that it forms a seal when it is in a user's mouth.

The lip flange portion 72 is generally flared to fit the spaced between a user's lips and teeth. This allows the unit to fit snugly against the teeth and at the same time allow the lips comfortably to draw over onto the respective outer lip surface or portion 74. The two respective lip portions flow in a contoured manner with respect to the user's mouth so as to generally fill somewhat the area of the space between the inner portion of the user's lips and the teeth.

Interiorly of the interior surface 76 of the mouthpiece portion 10 is an upper web or palate portion 80. The upper web 80 spans a portion of the palate of a user. The surface of the upper web 80 is configured to lie along a user's palate and generally conform to the interior portion of it. The palate portion or upper web terminates in a frontal area at the interior surface 76 of the mouthpiece lip portion 72 in a lateral opening 82 which can be seen in the various figures. The lateral opening allows for the teeth to project into the opening while at the same time allowing for the passage of gas between the upper and lower set of teeth.

A lower web portion or interior jaw portion 90 is shown having a surface which is contoured to the interior surface of a user's jaw or lower teeth. The lower web 90 is such where it is lesser in dimension as it extends inwardly to a user's mouth than the upper web. This serves to accommodate the more radical dropoff in the interior jaw region at the lower teeth. The lower web 90 or jaw contacting web is such wherein the interior surface 94 is contoured to engage a user's lower teeth and jaw interior surfaces.

Figure 2:
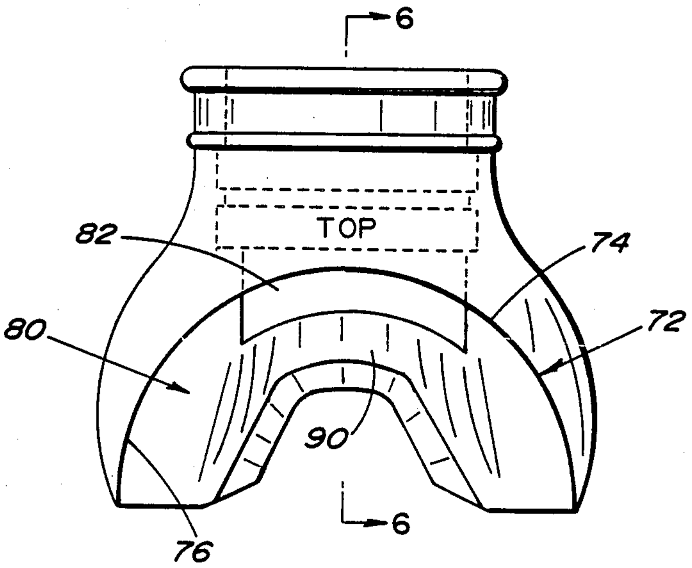
FIG. 2 shows a top plan view of the second stage regulator mouthpiece looking downwardly upon the showing of FIG. 1.
Figure 3:
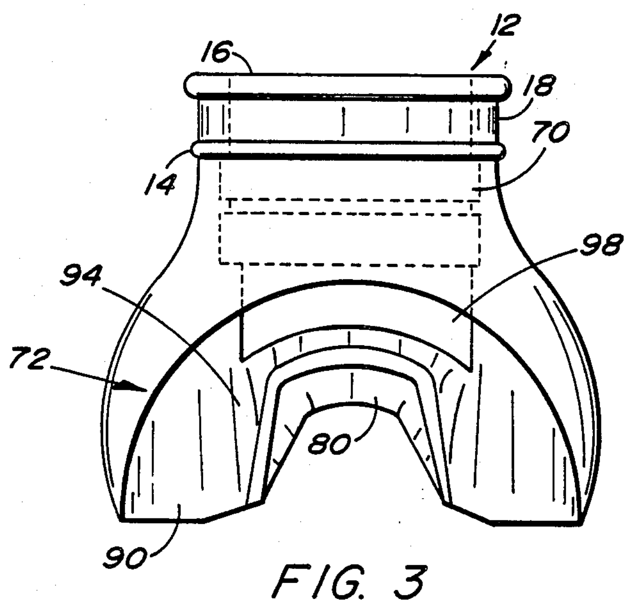
FIG. 3 shows a bottom plan view looking upwardly at the view shown in FIG. 1.
Figure 4:
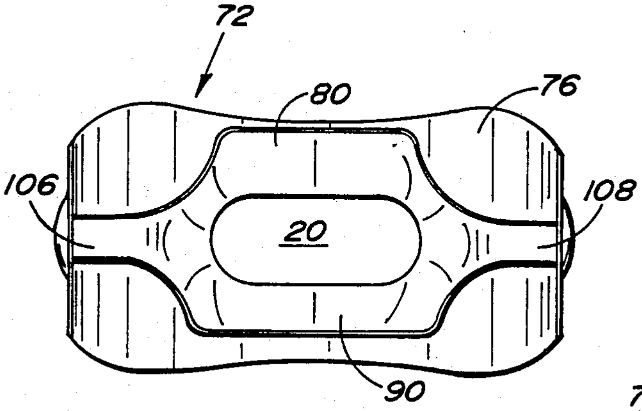
FIG. 4 shows an end view of the regulator mouthpiece as seen in the direction of lines 4—4 of FIG. 1.
Figure 5:
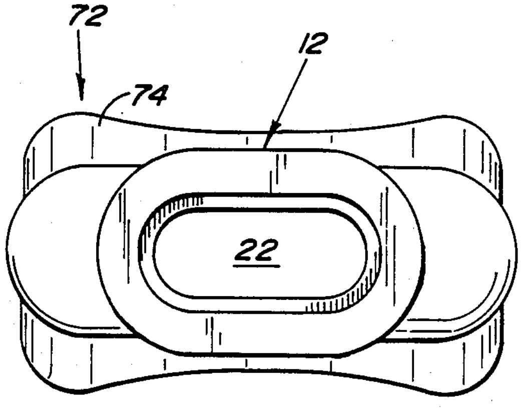
FIG. 5 shows an end view of the regulator mouthpiece as seen in the direction of lines 5—5 of FIG. 1.
Figure 6:
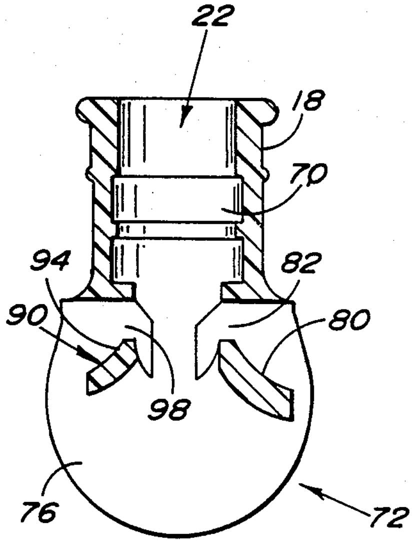
FIG. 6 shows a sectional view of the regulator mouthpiece as sectioned along lines 6—6 of FIG. 2.

The lower web 90 also has a lateral space 98 through which the front of the lower teeth can pass. The space 98 is such wherein it accommodates the teeth in the same manner as the space 82 so that the respective teeth overlie each other a seen through the spaces 82 and 98. This can be seen clearly in FIGS. 2 and 3 showing the fact that the spaces 82 and 98 extend directly into each other and are fundamentally in overlying relationship. The web 90 as can be seen in FIG. 3 underlies the upper web 80 to a significant degree and permits the radical dropoff in the manner as shown in the figures.

Figure 9:
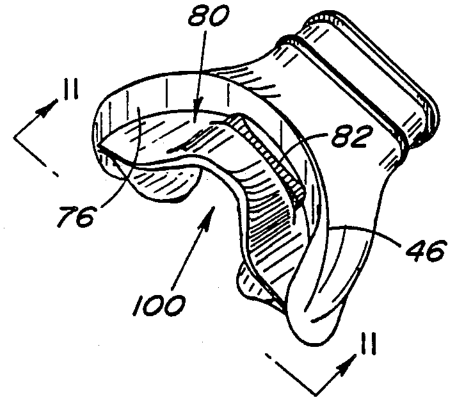
FIG. 9 shows a perspective view of an alternative and preferred embodiment of the regulator mouthpiece of this invention.
Figure 10:
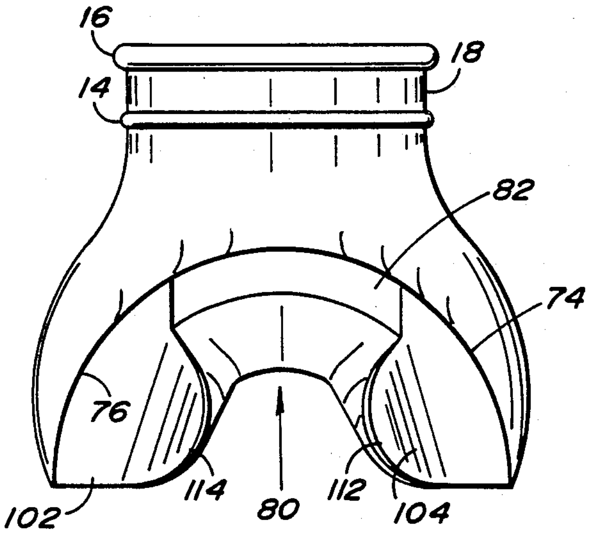
FIG. 10 shows a bottom view looking upwardly from the view shown in FIG. 9.
Figure 11:
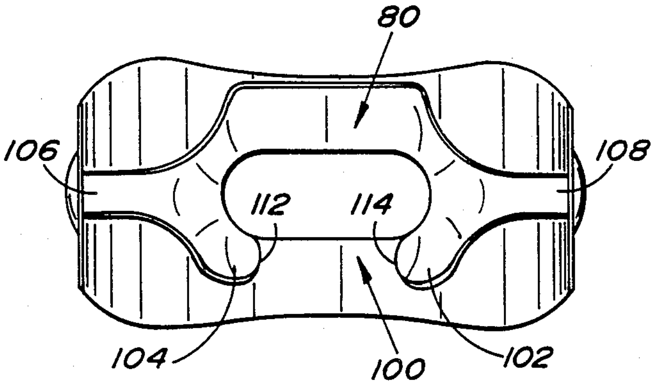
FIG. 11 shows an end view of the regulator mouthpiece as seen in the direction of lines 11—11 of FIG. 9.

Looking more particularly at FIGS. 9 through 11, an alternative and in many instances preferred embodiment is shown. In looking at these figures, it can be seen that the outer surfaces 74 of the lip flange 72 is seen with the inner surface 76 which engages a user's teeth. Both are configured in the same manner as the prior showings. The upper web 80 is also shown which passes against the palate. This upper web 80 also incorporates the opening 82 as seen in the prior figures. The opening 82 allows for the teeth to engage the mouthpiece while the surface of the web 80 extends across the interior palate of a user.

The lower web 90 has been shown with a split area 100. This split area 100 provides two respective tabular portions 102 and 104. The tabular portions 102 and 104 are fundamentally tabs which extend downwardly along the inner jaw surface in a steep manner in the same manner as the slope shown by the lower web 90 in FIGS. 1 through 8. The split area 100 or space allows for the tongue to move more freely while at the same time providing for a greater amount of air to be delivered into a user's mouth.

Both of the respective embodiments of FIGS. 1 through 7 and 9 through 11 cause the respective upper and lower webs 80 and 90 and tabular portion 102 and 104 to terminate in a thickened interfacial connecting web or flange. This is formed on either side as interconnecting web 106 and 108 of the two respective portions. These interconnecting webs 106 and 108 are of the same thickness and generally surround the interface between the respective upper and lower teeth. They extend and stop at the openings 82 and 98 respectively. However, it should be kept in mind that the showings of FIGS. 9 through 11 do not have the lower opening 98 inasmuch as the tabs 102 and 104 extend in such a manner as to be spaced by a gap or space 100 between the two tabs 102 and 104.

The space between tabs 102 and 104 can be provided in any suitable manner. Suffice it to say, in this particular embodiment they are shown interfaced by rounded portions 112 and 114 of the tabs 102 and 104. This allows for a ready accommodation of the teeth and the passage of the tongue into the area while at the same time maintaining sufficient air passage.

The entire mouthpiece area 10 is such wherein the showing of FIGS. 9 through 11 provide for the dropoff at the surface of the tabs 102 and 104 to conform to the interior jaw area of a user. This angular declination along the interior jaw area overlying the inside of the teeth is of a steeper and more angular departure from the axial line of the passage 22 and axis of the entire invention than web 80. Thus, it can be relatively defined that the upper web or palate portion 80 is of a lesser angular inclination from the axis of the mouthpiece than the lower surface defined bý tabs 102 and 104 or lower web 90. This varied angular inclination of the upper portion 80 and declination of the lower portion or web 90 or tabs 102 and 104 provide for the respective inclination and declination that maintains the mouthpiece in a configured manner against the palate of a user and the inner jawbone on the lower interior surface of the jaw and teeth.

Figure 8:
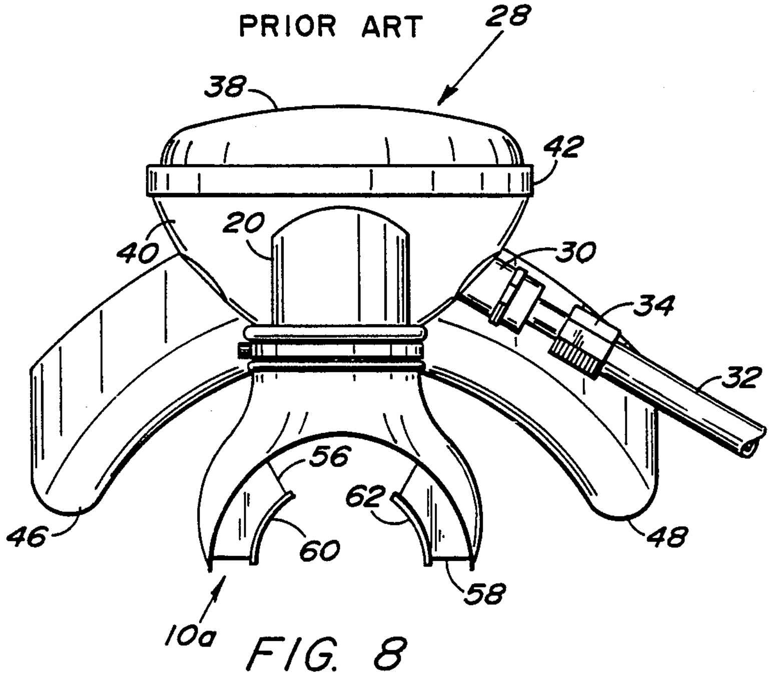
FIG. 8 shows a second stage regulator with a top plan view showing of a prior art mouthpiece attached thereto.

The overall configuration is such wherein it allows for this orientation to be configured and retain the mouthpiece section 10 in a comfortable manner. This is true not only within the lips of a user as in the prior art but also within an interfacing orientation against the palate and lower jaw area. As can be understood, the prior art as seen in FIG. 8 is significantly different and does not allow for a resting of the mouthpiece interior area against the palate and the interior of the jaw as well as the teeth. To the contrary, it completely relies upon the gripping of one's teeth against the surfaces 56 and 58 and securement against the flanges 60 and 62. This has been found to be tiresome and eminently fatiguing to a user. This is due to the fact that the weight of the second stage regulator such as regulator 28 creates a great degree of fatigue by the requirement of being gripped at the interface of the teeth at tabs 56 and 58.

This invention overcomes the foregoing problems by allowing for a contoured seating of the mouthpiece against the palate, the lower jaw area and interior tooth surfaces. It also accommodates the ability of the teeth to be seated within the axial passage 22 through the respective spaces 82 and 98 or in the alternative the space 100 between tabs 102 and 104.

The mouthpiece can also be molded or connected to a snorkel. In such a case, the tube or conduit portion 12 is molded or formed to a snorkel. In this manner, a snorkel provided with the mouthpiece functions to provide all the favorable features of the mouthpiece.

As a consequence of the foregoing, this invention should be read broadly in light of the following claims.

I claim:

1. A mouthpiece for a second stage breathing gas regulator comprising:

conduit means adapted for connection to an outlet of a second stage regulator so that gas being regulated by said second stage regulator can pass through said conduit means as well as exhaust from a user's mouth through said conduit means;

a mouthpiece portion extending from said conduit means said mouthpiece portion having a curved upper lip flange adapted generally for conforming to the interior region of a user's mouth between the upper teeth and the user's upper lips and a curved lower lip flange adapted generally for conforming to the interior region of a user's mouth between the user's lower teeth and the inner lower lips respectively;

said upper lip flange and said lower lip flange being joined to each other in a region intermediate between them;

each said upper flange and said lower flange including a frontal portion substantially coextensive with said conduit means and two opposed lateral portions extending from said frontal portion;

an upper interior web joined to and extending from said region between said upper and lower lip flanges, and being anatomically shaped for contact with at least part of the inside surfaces of at least the frontal upper teeth of a user and for extension at least partly in contact with a user's palate;

a lower web joined to and extending from the region between said upper and said lower lip flanges, said lower web being anatomically shaped for contact with at least a portion of the inside surfaces of the lower teeth of a user and for extension at least partly in contact with a user's interior lower jaw portion; and each said upper web and said lower web including a frontal portion substantially coextensive with said conduit means and two opposed lateral portions extending from said frontal portion.

2. The mouthpiece as claimed in claim 1 further comprising:

an opening within said frontal portion of said upper web through which at least a portion of a user's upper teeth can extend.

3. The mouthpiece as claimed in claim 1 further comprising:

an opening within said frontal portion of said lower web through which at least a portion of a user's lower teeth can extend.

4. The mouthpiece as claimed in claim 2 further comprising:

an opening within said frontal portion of said lower web through which as least a portion of a user's lower teeth can extend.

5. The mouthpiece as claimed in claim 4 wherein:

said conduit means includes a flange sealing means for seating to the second stage regulator.

6. The mouthpiece as claimed in claim 1 wherein:

said lower web is split and which comprises two laterally opposed, spaced apart tabular members which are anatomically shaped for contact with at least a portion of the inside surfaces of the lower lateral teeth of a user, and for extension at least partially in contact with the inside lateral lower jaw region of a user, said tabular members being spaced from said conduit means to provide a passage therebetween for a user's tongue.

7. The mouthpiece as claimed in claim 6 wherein:

said interior upper and lower lip flange contact surfaces have a relatively smooth curvilinear surface to fit against a user's teeth.

8. A second stage regulator mouthpiece having a conduit connected thereto for receipt of a second stage regulator for the passage of gas through said conduit wherein the improvement comprises:

a mouthpiece section attached to said conduit having a pair of upper and lower lip flanges wherein said lip flanges conform to the interior region between a user's lips and a user's teeth;

said upper lip flange and said lower lip flange being at least partly joined to each other in a region intermediate between them;

each said upper flange and said lower flange including a frontal portion substantially coextensive with said conduit means and two opposed lateral portions extending from said frontal portion;

an upper web which conforms generally to a user's palate which extends from and is substantially coextensive with said region between said upper and lower lip flanges;

a lower web having a pair of spaced apart tab portions which conform generally to the interior teeth and jaw regions of a user and which extend from the outer lateral region between said upper and lower lip flanges for contact with the interior lateral lower teeth of a user and spaced apart sufficiently to allow the passage of gas into a user's mouth.

9. The mouthpiece as claimed in claim 8 further comprising:

an interfacial web portion which joins said upper web and said lower tabs against which the teeth of a user can be seated.

10. The mouthpiece as claimed in claim 9 further comprising:

an opening in the upper web through which the teeth of a user can extend.

11. The mouthpiece as claimed in claim 10 wherein:

said opening is in said frontal portion of said web for receiving a frontal portion of a user's teeth.

12. The mouthpiece as claimed in claim 11 wherein:

said conduit means is configured and adapted to extend over an air tube of a second stage regulator and further comprising flange means for receiving a clamp for holding said conduit means to the tube of said second stage regulator.

13. The combination of a second stage regulator having a housing, valve means within said housing for conducting gas into said second stage regulator, means connected to said second stage regulator for receiving intermediate pressure, means for exhausting gas from said second stage regulator, and gas tube means extending from said second stage regulator to a mouthpiece, said mouthpiece comprising:

conduit means for connection to the gas tube means of said second stage regulator;

upper and lower lip flanges extending from said conduit means in a curved arcuate configuration for conformation respectively to the area between the inner surface of the lips and the outer portion of the teeth of a user;

said upper lip flange and said lower lip flange being being at least partly joined together in a region intermediate between them;

each said upper flange and said lower flange including a frontal portion substantially coextensive with said conduit means and two opposed lateral portions extending from said frontal portion;

an upper interior web which conforms generally to a user's palate which extends from and is substantially coextensive with said region between said upper and lower lip flanges;

at least a partial interior lower web extending form the region between said upper and lower lip flanges for contact with the interior lateral lower teeth of a user;

each said upper web and said lower web including a frontal portion substantially coextensive with said conduit means and two opposed lateral portions extending away from said frontal portions.

14. The combination as claimed in claim 13 wherein:

said lower web is formed of two spaced apart generally rounded tabs which conform generally to the interior lower teeth and jaw regions of a user and which extend from the outer lateral region between said upper and lower lip flanges for contact with the interior lateral lower teeth of a user.

15. The combination as claimed in claim 14 wherein:

said upper web and lower tabs are joined in the region between said upper and lower lip flanges from which said upper web and lower tabs extend.

16. The combination as claimed in claim 15 wherein:

said upper web has an opening through which the teeth of a user can extend.

17. The combination as claimed in claim 16 wherein:

said opening in said upper web is within the frontal portion.

18. The combination as claimed in claim 13 further comprising:

an opening within the lower web through which the teeth of a user can extend.

19. The combination as claimed in claim 18 wherein:

said upper web has an opening through which the teeth of a user can extend.

20. A snorkel mouthpiece comprising:

conduit mean adapted for connection to an outlet of a snorkel so that gas being conducted by said snorkel can pass through said conduit means as well as exhaust from a user's mouth through said conduit means;

a mouthpiece portion extending from said conduit means said mouthpiece portion having a curved upper lip flange adapted generally for conforming to the interior region of a user's mouth between the upper teeth and the user's upper lips and a curve lower lip flange adapted generally for conforming to the interior region of a user's mouth between the user's lower teeth and the inner lower lips; respectively;

said upper lip flange and said lower lip flange being joined to each other in a region intermediate between them;

each said upper flange and said lower flange including a frontal portion substantially coextensive with said conduit means and two opposed lateral portions extending from said frontal portion;

an upper interior web joined to and extending from said region between said upper and lower lip flanges, and being anatomically shaped for contact with at least part of the inside surfaces of at least the frontal upper teeth of a user and extending at least partly in contact with a user's palate; and, a lower web joined to and extending from the region between said upper and said lower lip flanges, said lower web being anatomically shaped for contact with at least a portion of the inside surfaces of the lower teeth of a user and extending at least partly in contact with a user's interior lower jaw portion; and, each said upper web and said lower web including a frontal portion substantially coextensive with said conduit means and two opposed lateral portions extending from said frontal portion.

21. The mouthpiece as claimed in claim 20 further comprising:

an opening within said frontal portion of said upper web through which at least a portion of a user's upper teeth can extend.

22. The mouthpiece as claimed in claim 20 further comprising:

an opening within said lower web through which a user's lower teeth can extend.

23. The mouthpiece as claimed in claim 21 further comprising:

an opening within said lower web through which a user's teeth can extend.

* * * * *